Figure 1:
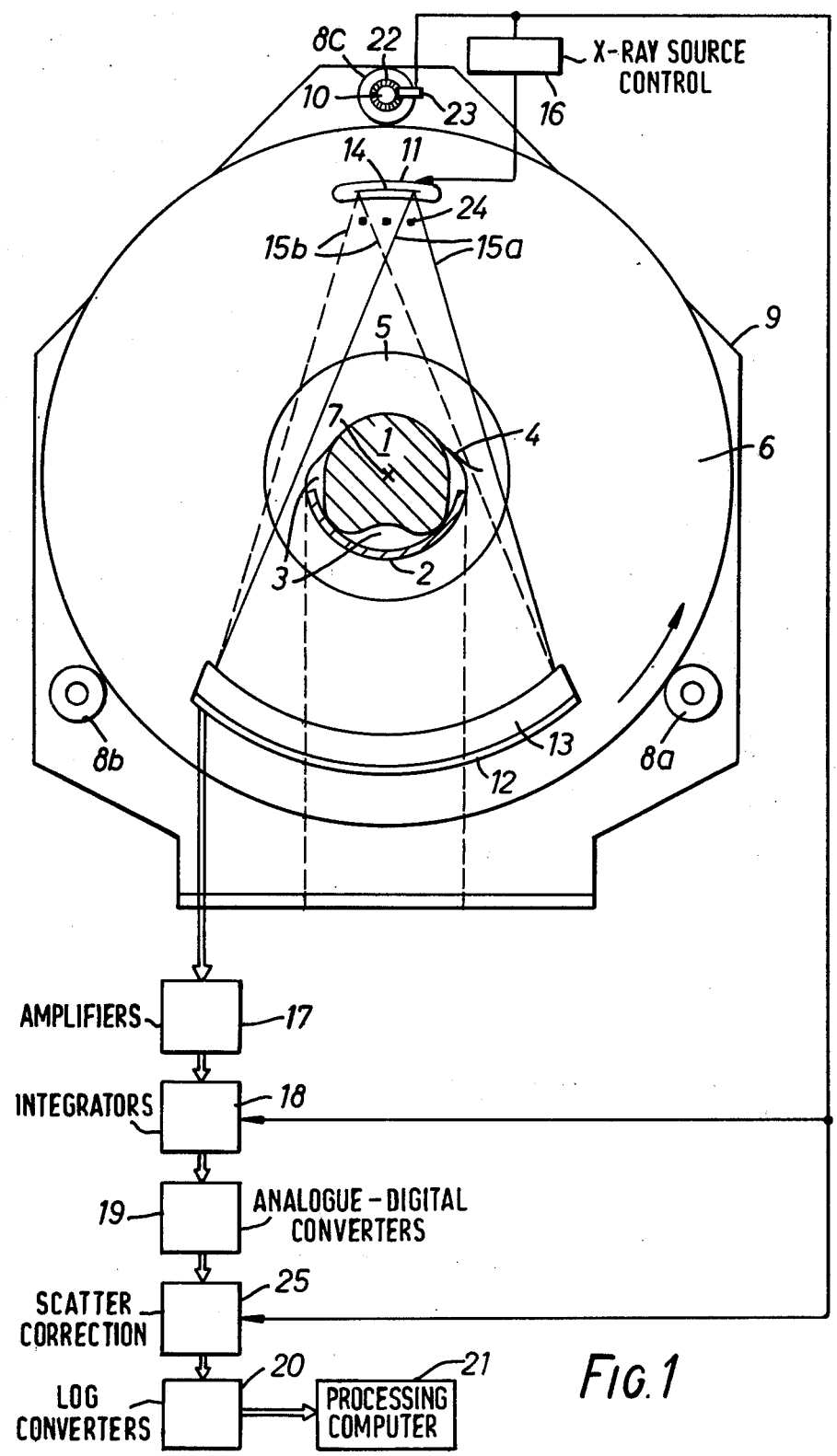

United States Patent [19]
Oliver

[11] 4,114,041
[45] Sep. 12, 1978

[54] RADIOGRAPHY

[75] Inventor: Colin Charles Oliver, Langley, Slough, England

[73] Assignee: EMI Limited, Hayes, England

[21] Appl. No.: 765,422

[22] Filed: Feb. 3, 1977

[30] Foreign Application Priority Data

Feb. 5, 1976 [GB] United Kingdom ............... 4546/76

[51] Int. Cl.² ............................................. G03B 41/16
[52] U.S. Cl. .............................. 250/445 T; 250/505; 250/514
[58] Field of Search .................... 250/445 T, 505, 514

[56] References Cited
U.S. PATENT DOCUMENTS 3,937,965  2/1976  Vasseur ........................... 250/445 T Primary Examiner—Craig E. Church
Attorney, Agent, or Firm—Cooper, Dunham, Clark, Griffin & Moran

[57] ABSTRACT

In a radiographic apparatus for deriving a representation of the variation of absortion of radiation in a slice of the body of a patient, data are derived which represent the intensity of radiation transmitted through the body. Detectors arranged to receive the transmitted radiation also receive further radiation, scattered within the body, which can cause errors in the final representation. The invention interposes occulting means between the radiation source and some detectors to obtain data representing only scatter to correct the transmission readings of the other detectors. The same detectors may serve both purposes at different times.

15 Claims, 3 Drawing Figures

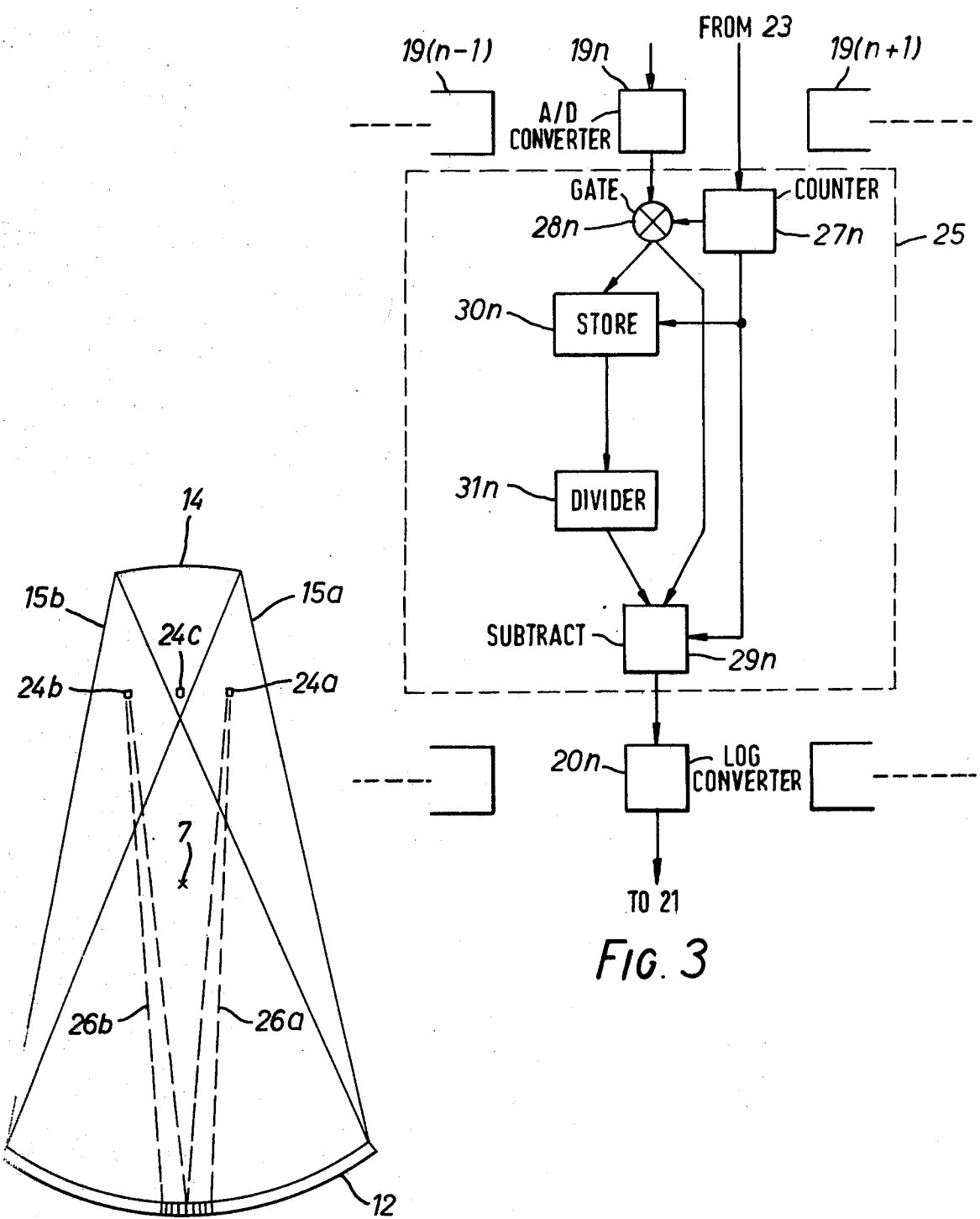

RADIOGRAPHY

This invention relates to a method of and apparatus for constructing a representation of the variation of absorption, with position across a planar slice of a body, with respect to penetrating radiation.

A method of and apparatus for constructing such a representation is described in U.S. Pat. No. 3,778,614. According to one example given in that specification a scanning movement is imparted to a suitable source of radiation to provide a plurality of substantially parallel pencil beams of radiation at each of a plurality of inclinations in the plane of the slice. A suitable detector is scanned in a corresponding manner to provide a measure of the absorption suffered by each of the beams in passing through the body. These measurements of absorption are then processed to provide a distribution of absorption coefficients for the planar slice. To provide the required plurality of beams the source and detector are reciprocated in the plane of the slice and orbited in steps about a common axis normal to that plane.

An alternative processing method involving a form of convolution is further described in U.S. Pat. No. 3,924,129.

A variation of the method and apparatus, capable of faster scanning rates, is described in U.S. Pat. No. 3,937,963. In that arrangement a fan shaped spread of radiation is provided having a sufficient angular spread to encompass the entire region of interest in the body. A plurality of detectors distributed across the fan on the other side of the body provide determinations of the intensity of radiation transmitted through the body along a plurality of beams within the spread.

In that case a complete scan can be effected solely by orbiting the source and detectors about a common axis normal to the plane of the slice.

A development of that apparatus, for which the effect of sensitivity variations between the detectors can be reduced, is described in United States Application No. 733,941. However in certain circumstances errors may arise due to the detection of scattered radiation by the detectors.

It is an object of this invention to provide a further development of the apparatus for which such errors are reduced.

According to the invention there is provided apparatus for examining a slice of a body by means of penetrating radiation; the apparatus including a source arranged to project the radiation from a substantially point origin through a region including the slice, detector means sensitive to the radiation and arranged to receive the radiation after passage through the region, means adapted to cause the source to project the radiation through the region from a plurality of different positions in relation to the body to provide output signals each relating to the intensity of radiation transmitted through the region along a respective one of a plurality of different beam paths, means adapted to cause the detector means to provide, at predetermined times, further output signals relating substantially only to radiation scattered in the region and means for utilising the further output signals to reduce errors, in the first mentioned output signals, caused by radiation scattered within the region.

In order that the invention may be clearly understood and readily carried into effect an example thereof will now be described with reference to the accompanying drawings of which, FIG. 1 shows an apparatus in accordance with the invention, FIG. 2 is a diagram used to explain the operation of the apparatus of FIG. 1 and, FIG. 3 is a block diagrammatic circuit suitable for implementing the invention.

Referring to FIG. 1 there is shown apparatus in accordance with one example of the invention. A body 1, to be examined, is shown in transverse section supported on a suitably shaped bed 2, which is also shown in transverse section. A material 1, having an absorption similar to that of body tissue, is positioned between the body 1 and the bed 2 and may be extended partly about the body to present an approximately circular cross-section to the radiation. A retaining strap 4 is provided to hold the body firmly in the desired position.

The bed 2 and the body 1 are inserted into an aperture 5 in a rotatable member 6 so that a desired part of the body is centred in the aperture. The rotatable member 6 is capable of rotation about an axis 7, longitudinal of the body in this example and perpendicular to the paper. For that purpose it is supported by three gear wheels 8 *a, b, c* which engage with gear teeth, not shown, cut into the periphery of member 6. The gear wheels 8 are journalled in a main frame 9 of the apparatus. The main frame 9 may take any form suitable to support the apparatus and to allow the rotation. Gear wheel 8c is driven by a motor 10, also mounted on the main frame.

The rotatable member 6 also carries a source 11 of x-radiation, a bank of detectors 12 and associated collimators 13. The detectors, which in a typical embodiment number 200, can be of any suitable type, for example scintillation crystals with associated photomultipliers or photodiodes.

The source 11 is of the type which includes an elongated target/anode 14 and provides a fan-shaped spread 15 of x-radiation from a substantially point origin which can be scanned by electronic means from the position 15*a* to the position 15*b* shown. In this example the corresponding scan of the substantially point origin of the x-rays along target 14 is of the order of three centimeters although it may be more or less if desired. The collimators have longitudinal axes which intersect at the centre of the anode 14. As an alternative a scan of the point origin can be provided by using a rotating anode X-ray tube with a suitably shaped anode.

In this example the x-ray source is placed of the order of fifty centimeters from the central axis 7 with the detectors 12 being placed a further fifty centimeters on the opposite side of axis 7 so as to intercept the radiation of fan 15 for any position of the point of origin of the x-rays in its lateral scan along target 14. In practice however the distances from source to axis 7 and from detectors to axis 7 may be unequal. The collimators 13 are of dimensions which allow interception of the x-rays at all times while preventing the reception of scattered radiation to the greatest degree practically possible.

Disregarding for the moment the rotary motion referred to hereinbefore, the arrangement is such that the point of origin of the x-rays is scanned steadily along target 14 taking the fan of x-rays 15*a* to 15*b*, and is rapidly returned to the starting point before repeating the scan. This is achieved by a sawtooth waveform from an x-ray source control unit 16, being used to deflect the incident electrons on the surface of target 14. During the time of one such scanning movement each detector of array 12 provides an output indicative of the intensity of radiation incident thereon. These outputs are amplified in amplifiers 17 and then input to integrators 18. There the outputs are integrated over periods determined by pulses the origin of which will be described hereinafter. In this example the timing of the pulses is such that there are thirty integration periods in the time of one lateral scan of the x-ray fan from 15a to 15b. Thus each detector measures radiation in effect along thirty narrow beam paths joining that detector with thirty equally spaced positions along target 14. The paths are, of course, of width determined by the integration intervals and are of a shape determined by the geometry of scanning movements in those intervals. For the purposes of illustration, however, they may be considered to be represented by single lines which are in fact their central lines. The lines illustrating the extremes of fan 15 are in fact the centre lines of the extreme beams of the fan. Disregarding for the moment circuits 25, signals representing the intensity of radiation received along such paths are converted to digital form in converters 19 and to logarithmic form in converters 20 for output for further processing in a processing computer 21. It will be understood that one amplifier 17, integrator 18, A/D converter 19 and log converter 20 is provided for every detector, all operated in synchronism. The processing computer is effective to sort the signals into sets representing absorption along sets of parallel paths as explained in the said and then to process them by a suitable method such as that described in the said U.S. Pat. No. 3,924,129 to provide the desired representation. In alternative a convolution series applicable to a fan shaped distribution of paths can be used to avoid the necessity of sorting into sets of parallel paths. It will be understood that, for the processing described in U.S. Pat. No. 3,778,614 no special distribution of paths is required. All of the circuits referred to hereinbefore are of well known construction. The processing may take any alternative form suitable to the form of the apparatus, including the form described in the said U.S. Pat. No. 3,778,614. Furthermore the preprocessing circuits can be rearranged as convenient. In one arrangement proposed the outputs of the integrators are multiplexed to a reduced number of A/D converters and arrangements are made for the processing computer to effect log conversion.

In order to achieve the desired effect motor 10 provides a continuous motion of rotatable member 6 and all of the equipment mounted thereon, about axis 7 and therefore about the body 1 of the patient on bed 2. The desired motion is such that the angular motion of the X-ray fan 15 during a scan across anode 14 complements the angular motion of the rotation. In that time each detector provides data relating to a series of beam paths at rapidly increasing angular displacement. At the time of the fly back of the point of origin the fan 15 returns to the position which it would have reached in the presence of orbital motion only and commences to examine a further series of beam paths at least partly interposed between the earlier set.

It will be understood that the rotary motion must be properly related to the X-ray scan and the operation of integrators 18. For this purpose the rotary motion is chosen to be the controlling factor in this example. The shaft of gear wheel 8c is provided with a circular graticule 22 in the form of a translucent ring carrying engraved lines. These lines can interrupt a light path between a light source and photocell, indicated generally at 23, mounted on main frame 9 so that the photocell provides pulses indicative of the movement of member 6. These pulses are supplied both to the X-ray source control 16 and integrators 18 and may also be supplied to a control computer controlling the data processing if desired. Other sources of such timing pulses may of course be used.

The apparatus thus far described is essentially the same as that described in the said Application No. 733,941 and the operation required to achieve the final representation is the same as that described therein. The same form of apparatus is used in the arrangement of United States Application No. 630,779 which is incorporated herein by reference, and the method of operation and method of reconstruction described therein can be used with this invention. In this example there are, however, also included a plurality of occulting members 24 mounted on rotatable member 6. Members 24 are made of a material, such as lead, which is substantially opaque to the radiation and are intended to prevent direct radiation falling on at least some of the detectors for part of each lateral scan. This, of course, reduces the number of parallel beam paths examined by those detectors during one lateral scan. However the number of paths so examined is sufficiently in excess of that required to obtain a satisfactory representation of absorption, so that such a reduction in the measured data does not effect the final accuracy seriously. It will be understood, moreover, that while a detector is shielded from direct radiation it can still detect scattered radiation which is not obstructed by the respective member 24. The scatter reading thus obtained is then subtracted from the direct readings obtained at the same, or substantially the same, time or position, to ensure that they relate to a greater extent only to direct radiation along the desired beam path. Occulting members 24 may be used in several different ways in accordance with the principles of the invention. They may be placed so that every detector is obscured at some point in each scan so as to obtain an individual scatter measurement. Alternatively they may be placed to obscure each detector several times during each scan so that the scatter measurements relate more closely in position to the direct measurements to be corrected. As a further variation they may be placed so as to obscure only some detectors in each scan to obtain typical measurements of scatter for use by the other detectors. For the purpose of making the necessary corrections, scatter correction circuits 25 are additionally provided between A/D converters 19 and log converters 20. Circuits 25 will be described in greater detail hereinafter.

A typical arrangement of occulting members 24 is shown in FIG. 2. It will be seen that for x-ray fan position 15a a member 24a provides a shadow region 26a occulting in this example four detectors. It will be understood that the number of detectors obscured at any time by a member 24 may be varied as desired. Furthermore since the occulting members have a finite size, and the point source is also a finite size, there is in practice a region of penumbra outside of the shadow shown for which the detector output signals cannot be used since they are at least partly shaded by a member 24. The number of detectors thus unusable is known as a function of the geometry of the apparatus. Also in practice only the centre two detectors of the four in shadow are completely occulted throughout an integration interval and are thus available for use in determining scatter. In the course of a scan of the x-ray fan from 15a to 15b member 24a obscures detectors progressively further to the right on array 12. Similarly, at an appropriate point, member 24b commences to obscure detectors at the left of the array and the corresponding shadow region 26b moves progressively right to the position shown. The central member 24c, although not providing any shadow region for the fans shown, does in a complete scan obscure all detectors with a shadow region moving progressively to the right.

Since the shadow regions obscure four detectors they correspondingly obscure each detector for four integration intervals. Each scatter measurement can therefore be a mean of four different measurements although in practice only two may be usable as mentioned hereinbefore.

One possible arrangement of the circuits 25 is shown in FIG. 3 although many variations will be apparent to those skilled in the art.

The circuits 25 comprise, in this example, a plurality of individual circuits of which a typical nth circuit, receiving data from A/D converter 19n, is shown in FIG. 3.

It will be understood that, since the geometry of the apparatus including the placing of members 24 is known, the sequence of data signals and the position in that sequence of data representing scatter will be known as a design parameter. The circuit is therefore controlled by a counter 27n which receives the pulses from the photocell in unit 23. Counter 27n counts these pulses which, since they also control integrators 18, represent integration intervals and, after predetermined counts provides output pulses which form instructions to the other units to be described. The data from A/D converter 19n are provided to a gate 28n which normally routes them to a subtractor 29n. However at the correct time, as determined by pulses from counter 27n, gate 28n routes a suitable number, in this example two of the four "shadow" signals to a store 30n where they are additively stored. In addition the gate 28n discards signals originating from detectors which are only partially occulted by members 24. For all of these signals the further processing is organised to expect no data output from channel n. At all other times the data routed direct have subtracted from them in 29n the last stored value in store 30n which represents the most recent estimate of the scattered radiation. In this example, since the data in store 30n are the sum of two values, they are divided by two in a divider 31n before subtraction.

If desired the control of circuits 25 may be provided directly by a control computer controlling the processing, which may receive the pulses from the photocell. In general it should be understood that many of the circuits shown independantly may be provided by a central digital computer or by other circuits to perform the same functions.

Other variations of the invention may be devised consistant with the principle of providing some output readings which are from detectors receiving only scattered radiation. For example if it is not desirable to interrupt any of the radiation passing through the body 1, other detectors may be provided at the extremes of array 12 so that they are not intercepted by fans 15 but do receive some scattered radiation. These may be used to provide, in each integration interval, estimates of the scattered radiation present for subtraction from the outputs of the other detectors.

The invention may also be used in arrangements in which a large array of stationary detectors is used. In such applications a fan-shaped spread of radiation can be scanned relative to the detectors, either in a lateral or orbital scan, so that fixed occulting members can give a scatter estimate.

It is not necessary for all purposes to correct the direct output readings for scatter. In an alternative arrangement on absorption distribution can be determined from the output reading for scattered radiation and subtracted from that determined for nonscattered radiation.

In a further alternative the scanning x-ray source may be replaced with a point source, such as a conventional rotating anode tube, and occulting members such as 24 may be mounted so as to move in relation to rotating member 6, e.g. by being fixed to main frame 9. That movement will then cause the source to pass behind successive such members to give the required scatter estimates.

In general the invention is not limited to x-ray equipment of the type shown in FIG. 1. It may be used in any similar equipment in which at least one detector receives, for at least part of the time of examination, radiation which is primarily scattered for correction of readings for radiation which should be primarily directly transmitted.

What I claim is:

1. Apparatus for examining a slice of a body by means of penetrating radiation, the apparatus including a source arranged to project the radiation through a substantially planar region including the slice, detector means sensitive to the radiation and arranged to receive the radiation after passage through the region, means for causing the source to project the radiation through the region from a plurality of different positions in relation to the body, means for deriving from the detector means output signals each relating to the intensity of radiation transmitted through the region along a respective one of a plurality of beam paths to a respective position in the plane of the region, means for deriving from the same detector means further output signals each relating substantially only to radiation scattered in the region and received by the detector means at a respective one of a plurality of positions in the plane of the region and means for utilising the further output signals to reduce errors, in the first mentioned output signals, caused by radiation scattered within the region.

2. An apparatus according to claim 1 wherein the means for utilising includes means for subtracting from an output signal a mean value of one or more further output signals obtained at substantially the same time or source position.

3. An apparatus according to claim 1 wherein the means for deriving said further output signals comprises one or more occulting means each arranged to shield at least a selected portion of the detector means at appropriate predetermined times from radiation which would otherwise be incident thereon after transmission along at least one direct path from the source.

4. An apparatus according to claim 3 including means providing a relative motion between the point of origin of the radiation and the occulting means so as to shield the detector means from radiation transmitted along different direct paths, relative thereto, at different times.

5. An apparatus according to claim 4 wherein the occulting means are fixed relative to the detector means.

6. An apparatus according to claim 4 wherein the point of origin of the radiation is fixed relative to the detector means.

7. An apparatus according to claim 4 wherein the occulting means are fixed relative to the body.

8. An apparatus according to claim 1 wherein said detector means comprises a plurality of adjacent detector devices and said source provides a fan-shaped spread of radiation arranged to simultaneously irradiate several of said detector devices.

9. An apparatus according to claim 3 wherein the means for utilising comprises means for using a further output signal, obtained when the detector means is shielded from radiation along a direct path, to correct for scattered radiation first mentioned output signals relating to radiation actually transmitted along the same path through the body.

10. An apparatus according to claim 3 wherein the means for utilising comprises means for using a further output signal, obtained when the detector means is shielded from radiation along a direct path, to correct for scattered radiation first mentioned output signals relating to radiation transmitted along paths within a predetermined distance, in relation to the body, of the shielded direct path.

11. Apparatus for examining a slice of a body by means of penetrating radiation, the apparatus including: a source arranged to project the radiation through a region including the slice; detector means including a plurality of detector devices sensitive to the radiation and arranged to receive the radiation after passage through the region; means for causing the source to project the radiation through the region from a plurality of different positions in relation to the body; means for deriving from the detector devices output signals, each relating to the intensity of radiation transmitted through the region along a respective one of a plurality of beam paths, for processing to derive a representation of the distribution of absorption, for the said radiation, of matter traversed by the radiation in the slice; means for causing at least some of the detector devices to provide at certain times the respective output signals relating to directly transmitted radiation and at other times further output signals which relate substantially only to radiation scattered in the region; and means for utilising the further output signals to reduce errors in the representation caused by components of the first mentioned output signals relating to radiation scattered within the region.

12. Apparatus for examining a slice of a body, the apparatus including: a source arranged to project the radiation through a region including the slice; means for causing the source to project the radiation through the region along a plurality of different direct paths at different orientations therein; detector means, comprising a plurality of detector devices sensitive to the radiation arranged to detect the radiation after passage through the region and to provide output signals representing the intensity of radiation received from the source along direct and scattered paths through the region; means for processing the output signals to provide a representation of the distribution of absorption of the radiation in at least part of the region; means for causing at least one of said detector devices to receive, for part of the time of the examination, radiation which is primarily scattered to provide further output signals representing the intensity of radiation received along scattered paths through the body; and means for utilising the further output signals to reduce the effect on the representation of components of the first mentioned output signals relating to radiation received along scattered paths.

13. A method of examining a slice of a body by means of penetrating radiation including the steps of: projecting radiation from a source through a region including the slice at a plurality of different orientations in relation to the body, determining the intensity of the radiation received at a plurality of positions outside the region after direct and scattered transmission through the region, shielding some of the said positions at predetermined times only from radiation transmitted along direct paths from the source, determining at said predetermined times the intensity of scattered radiation received at the said positions, and constructing a representation of the absorption of the radiation in the said slice, in a form substantially representative of radiation transmitted directly through the region, in response to the first and second mentioned determinations of intensity.

14. A method according to claim 13 including the steps of correcting the first mentioned determinations of intensity in view of the second mentioned determinations of intensity to provide further determinations more closely representative of the intensity of radiation directly transmitted to the respective positions and processing the further determinations to construct the said representation.

15. A medical radiographic apparatus comprising:
means defining a patient position and means disposed outside the patient position for generating penetrating radiation and projecting it along a region of space intersecting the patient position to emerge therefrom after suffering absorption and scattering by the matter through which it has travelled within the region;
means for moving the origin of the radiation in relation to the patient position so as to project the radiation through the region along a plurality of different direct paths, at different orientations therein;
means for detecting the radiation emerging from the patient position at positions intersecting said direct paths to provide first output signals representing the intensity of radiation received from the source at those positions along direct and scattered paths through the body;
occulting means for shielding the detecting means at some of said positions from radiation transmitted along the respective direct paths from the generating means to provide second output signals representative substantially only of radiation received from the source at said some positions along scattered paths through the body;
processing means for constructing a representation of the distribution of absorption characteristics, for the said radiation, of the matter traversed by the radiation within the said region in response to the first and second output signals.

* * * * *